United States Patent [19]

Webster et al.

[11] Patent Number: 5,043,491

[45] Date of Patent: Aug. 27, 1991

[54] MULTISTEP SYNTHESIS OF HEXAFLUOROPROPYLENE

[75] Inventors: James L. Webster, Parkersburg, W. Va.; Elrey L. McCann, Mendenhall, Pa.; Douglas W. Bruhnke, Landenberg, Pa.; Jan J. Lerou, Chadds Ford, Pa.; Leo E. Manzer, Wilmington, Del.; William H. Manogue, Newark, Del.; Paul R. Resnick, Wilmington, Del.; Swiatoslaw Trofimenko, Wilmington, Del.

[73] Assignee: E. I. Du Pont de Nemours and Company, Wilmington, Del.

[21] Appl. No.: 452,401

[22] Filed: Dec. 19, 1989

[51] Int. Cl.$^5$ .................. C07C 17/00; C07C 17/08
[52] U.S. Cl. .................. 570/157; 570/156; 570/165; 570/166; 570/168; 570/169
[58] Field of Search .............. 570/155, 156, 157, 168, 570/167, 175, 176

[56] References Cited

U.S. PATENT DOCUMENTS

| | | |
|---|---|---|
| 2,758,138 | 8/1956 | Nelson . |
| 2,900,423 | 8/1959 | Smith . |
| 2,970,176 | 1/1961 | Ten Eyck et al. . |
| 3,258,500 | 6/1966 | Swamer et al. . |
| 3,306,940 | 2/1967 | Halliwell . |
| 3,436,430 | 4/1969 | Hall . |
| 3,459,818 | 8/1969 | Ukihashi et al. . |
| 3,803,241 | 4/1974 | Stolkin et al. . |
| 3,865,885 | 2/1975 | Bruce . |
| 3,873,630 | 3/1975 | West . |
| 4,110,406 | 8/1978 | Anello et al. . |

FOREIGN PATENT DOCUMENTS

| | | |
|---|---|---|
| 1070929 | 6/1967 | United Kingdom . |
| 1077932 | 8/1967 | United Kingdom . |

OTHER PUBLICATIONS

Sheppard & Sharts, Org. Fluor. Chem., N.Y., 1969, pp. 74-81.

Hudlicky, Chem. of Org. Fluor. Compounds, 1962, pp. 481-489.

*Primary Examiner*—Alan Siegel
*Attorney, Agent, or Firm*—Donald W. Huntley

[57] ABSTRACT

The present invention relates to multistep syntheses of hexafluoropropylene from propane, propylene or partially halogenated acyclic three-carbon hydrocarbons. In all these syntheses the first step is a vapor-phase chlorofluorination of the starting material to the unsaturated chlorofluorocarbon $CF_3CClCCl_2$.

5 Claims, 1 Drawing Sheet

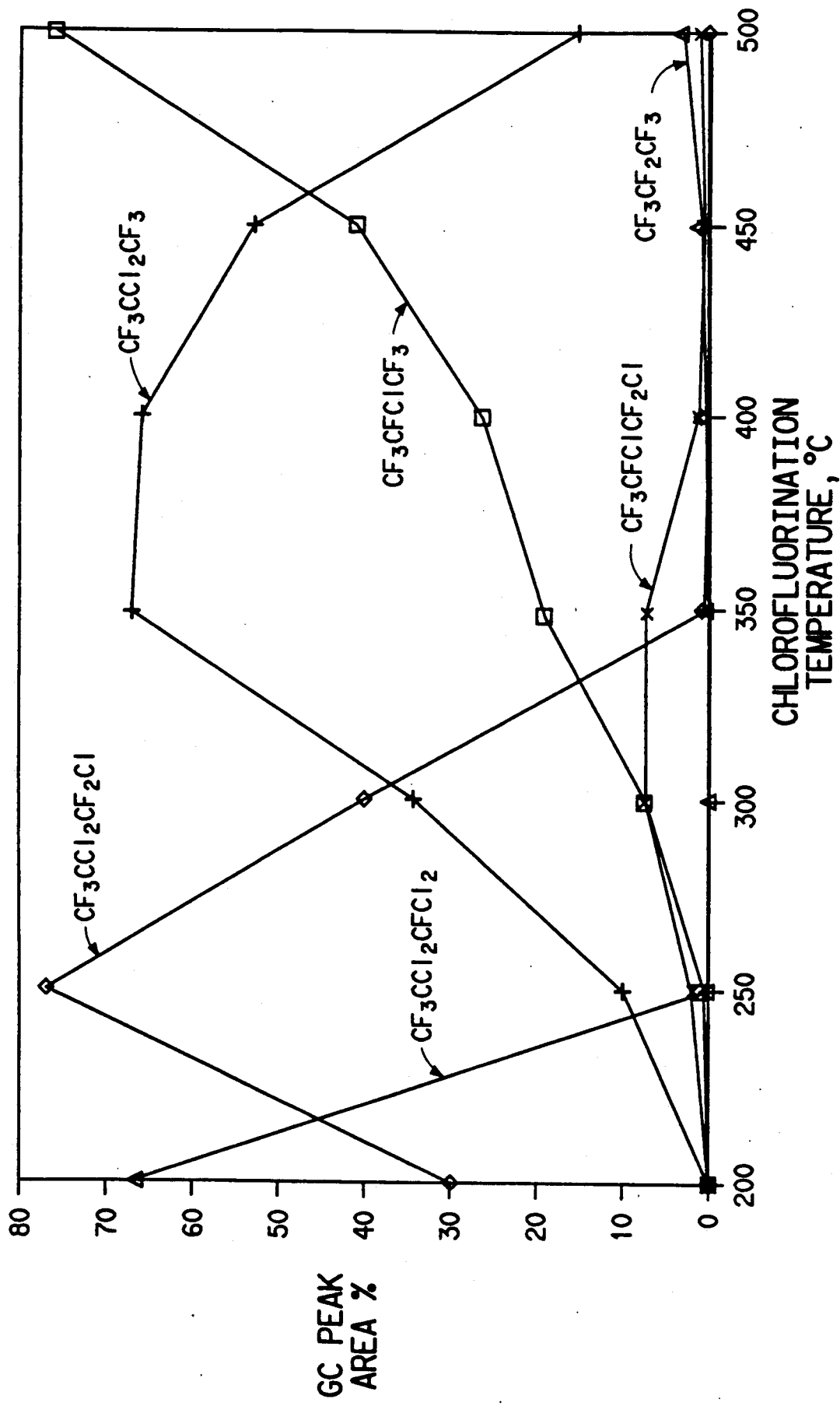

MULTISTEP SYNTHESIS OF HEXAFLUOROPROPYLENE

FIELD OF THE INVENTION

The present invention relates to multistep syntheses of hexafluoropropylene from propane, propylene or partially halogenated acyclic three-carbon hydrocarbons. In all these syntheses the first step is a vapor-phase chlorofluorination of the starting material to the unsaturated chlorofluoro-carbon $CF_3CCl=CCl_2$.

BACKGROUND OF THE INVENTION

Hexafluoropropylene has been prepared by the pyrolysis of tetrafluoroethylene. This process has several disadvantages. Tetrafluoroethylene, which is itself difficult to prepare and purify, is an explosive compound, which must be stored and handled with the greatest care. The pyrolysis of tetrafluoroethylene inevitably makes some perfluoroisobutylene as a by-product, and this compound is extremely toxic and is costly to remove and destroy. Another preparative method for hexafluoropropylene is to make it simultaneously with tetrafluoroethylene by pyrolysis of $CHClF_2$. The product also contains the toxic by-product perfluoroisobutylene, and the process provides a particular mixture of the two products, which may be different from the ratio of products desired by the user. Both of the above synthetic methods are carried out at high temperatures, so it is necessary to make the equipment from rare and expensive metals. Patents describing these processes include U.S. Pat. Nos. 3,873,630, 2,970,176, 3,459,818, 2,758,138, and U.S. Pat. No. 3,306,940.

U.S. Pat. No. 3,865,885 discloses a process which converts propylene to $CF_3$—$CCl=CCl_2$ in two steps, the first being the formation of isopropyl fluoride. The yield to $CF_3$—$CCl=CCl_2$ from isopropyl fluoride was 85%, using cobalt on carbon catalyst. Therefore, although the yield from propylene to $CF_3$—$CCl=CCl_2$ in two steps was not disclosed, it could not be higher than 85%.

UK 1077932 describes a process which gives 81% yield from propylene to $CF_3$—$CCl=CCl_2$ and recyclable intermediates, using a carbon catalyst.

U.S. Pat. No. 3,436,430 describes a process which provides chlorofluorinated propylene without a catalyst. The products were largely hydrogen-containing, even at 450° C. and 2.9 seconds catalyst contact time.

U.S. Pat. No. 2,900,423 relates to the synthesis of hexafluoropropylene by hydrogenation of $CF_3$—$CFCl$—$CF_3$ over a catalyst.

Fluorination (e.g. the reaction of a chlorinated hydrocarbon with 1-8 carbon atoms with HF to substitute F for Cl) is disclosed in U.S. Pat. No. 3,258,500.

SUMMARY OF THE INVENTION

The subject invention is a vapor phase process for the chlorofluorination of a feed containing at least one of the class consisting of propane, propylene and partially halogenated acyclic three-carbon hydrocarbons to make $CF_3$—$CCl=CCl_2$, followed by a process to convert the latter to hexafluoropropylene. The chlorofluorination step is carried out at elevated temperature in the presence of a metal-containing solid catalyst which is stable at reaction conditions. It is possible to recycle to the chlorofluorination step those intermediates which contain H or contain more than three Cl atoms.

The vapor phase chlorofluorination process to make $CF_3$—$CCl=CCl_2$, along with recyclable intermediates, gives a yield of at least 80%, preferably at least 90%, most preferably at least 95%. This process is conducted at elevated temperature in the presence of a catalyst, preferably a carbon-supported catalyst containing Fe, La, Rh, Zn, Ni, or Co, optionally promoted with a compound of Al, Ca, Cu, or K. Recyclable intermediates are those halogenated propylenes containing less than three F atoms or containing 1-5 H atoms.

The availability in high yield of $CF_3$—$CCl=CCl_2$ makes possible the synthesis of hexafluoropropylene from the above described feed.

The processes of this invention synthesize hexafluoropropylene without production of perfluoroisobutylene.

DETAILED DESCRIPTION OF THE INVENTION

Definitions

For the purpose of this disclosure:

Catalyst means a solid metal-containing catalytic salt or oxide as charged to the reactor. In many of the reactions described, the catalyst may undergo unknown changes in composition during pretreatment and reaction steps.

Contact time means the volume of catalyst charged to the reactor in ml, divided by the sum of all gas flow rates, in ml/sec, as measured at standard temperature and pressure.

Halogen means Cl and F.

Chlorofluorination means reaction of a feed containing at least one of the class selected from propane, propylene, and partially halogenated three-carbon acyclic compounds using a mixture of $Cl_2$ and HF.

In the following reaction sequence, conventional procedures may be used for reactant and product isolation and, if desired, recycle. Especially useful techniques are fractional distillation and partial condensation. It is possible not only to have a separate recovery system for each reaction, as is conventional, but it is possible to combine the product streams for product isolation, recognizing that it is important for the sake of safety to remove elemental hydrogen carefully from the hydrogenation product mixture before combining the stream with other product mixes that may contain elemental halogen.

Chlorine, HF, and HCl are separated by conventional methods. After removal of C-1 and C-2 by-products, the lowest boiling material is $C_3F_8$, which is a useful by-product; the next is hexafluoropropylene, which is the final product desired; the next lowest boiling among perhalocarbon intermediates is $CF_3$—$CFCl$—$CF_3$, which is used in the last step of the sequence. Unsaturated intermediates containing two or more chlorine atoms boil higher, and may be recycled with or without isolation.

The reaction sequence of the invention, including the final step resulting in hexafluoropropylene is:

a) Chlorofluorination of a feed containing at least one of the class selected from propane, propylene and partially halogenated three-carbon acyclic hydrocarbons to $CF_3$—$CCl=CCl_2$ b) $CF_3$—$CCl=CCl_2=HF=C_2\rightarrow CF_3$—$CFCl$—$CF_3$ c) Dehalogenation of $CF_3$—$CFCl$—$CF_3$ to hexafluoropropylene Chlorofluorination The catalysts which are effective for the chlorofluorination of the invention include selected compounds of the metallic elements. In use they may be in the form of their fluorides, oxyfluorides, chlorides, oxychlorides or oxides, but in the catalysts charged to the reactor they may be in the form of any compounds convertible to the above compounds under reaction conditions, such as pseudohalides and acid salts. They may be used either alone or in combination and in the presence or absence of a support such as, but not limited to, elemental carbon. Some minerals such as ceria and didymia contain mixtures or rare earths such as La, Sm, Nd, and Pr, and the salts of these minerals may be more practical to use than those of the pure elements.

Preferred catalysts for the production of $CF_3$—$CCl$=$CCl_2$ are compounds of Co, Co/Ca, Co/K, La, Rh, Zn, Fe, and Ni, with or without a catalyst support.

Most preferred catalysts for the production of $CF_3$—$CCl$=$CCl_2$ are compounds of Co (optionally promoted), La, and Fe.

In the catalytic chlorofluorination a temperature is employed of between 100° C. and 550° C. The preferred temperature is 175° C. to 475° C. The most preferred temperature is 200° C. to 400° C. The temperature used depends on the contact time chosen, the catalyst used, and the time the catalyst has been on stream.

In the chlorofluorination of propane/propylene the concentration of chlorine in relationship to propane/propylene may vary over a fairly broad range. Illustratively, mole ratios of chlorine to propane may be from 8 to 25, with a preferred range of 9 to 20 and most preferred range of 10 to 14. Mole ratios of chlorine to propane and/or propylene may be from 7 to 25, with a preferred range of 7 to 20 and most preferred range of 8 to 16.

In the chlorofluorination of propane/propylene the concentration of hydrogen fluoride in relationship to propane/propylene may vary over a fairly broad range. Illustratively, mole ratios of hydrogen fluoride to propane/propylene may be from 3 to 110, with a preferred range of 20 to 60, and most preferred range of 30 to 50.

The ratio of HF to chlorine can be varied over a broad range, 1–7 It is preferable to use lower HF:chlorine ratios, such as 1.7–4.3, most preferably 2.0–2.4, to make $CF_3$—$CCl$=$CCl_2$.

The above discussion of reactant ratios is based on the assumption that partially halogenated products are not being recycled. Normally, the large amounts of HF and $Cl_2$ are needed because the chlorofluorination reaction is so exothermic that it is desirable to operate adiabatically, with large amounts of cooled recycle HF and $Cl_2$ absorbing the heat given off by the chlorofluorination reaction.

In practice, it is convenient to recycle halocarbons that are not fluorinated to the desired degree, so that they will be converted to desired products. In addition, inert fluorocarbons such as $CF_4$ or $C_2F_6$ or $C_3F_8$ may be added and recycled to act as heat sink in an approximately adiabatic reactor. When recyclable intermediates or inert fluorocarbons are recycled to the chlorofluorination step, the weight of HF and $Cl_2$ in excess of the stoichiometric requirement can be reduced by approximately the weight of the halocarbons recycled.

In addition to propane, propylene, recycled intermediates, and mixtures thereof, it is also possible to feed to the chlorofluorination reaction a partially halogenated three-carbon acyclic compound. As just one example, 1,2-dichloropropane is readily available and can be used as the starting material, alone or with other feed materials specified above.

The reaction pressure is not critical and may be between 1 and 40 atmospheres. About 20 atmospheres is preferred to allow easy separation of HCl from the halocarbons without requiring compression.

The yield of desired products will be determined to a large extent by the temperature and contact time of the reactant materials with the catalyst. Contact times of the order of 300 seconds or less are suitable. Preferred contact times are 0.01 to 100 seconds. Most preferred contact times are 0.05 to 15 seconds.

When catalysts are relatively inactive or when mild chlorofluorination conditions of temperature, contact time, and reactant ratios are used, the products obtained still contain hydrogen, and are often unsaturated. Somewhat more strenuous conditions or more active catalysts give unsaturated products in which all hydrogen atoms have been replaced with halogen, such as the desired $CF_3$—$CCl$=$CCl_2$. Still more strenuous conditions or more active catalysts give saturated halocarbons which are rich in Cl. The most strenuous conditions or active catalysts give highly fluorinated propanes such as $CF_3$—$CFCl$—$CF_3$. In all cases, recycle of under-chlorofluorinated three-carbon intermediates results in further chlorofluorination and eventually in highly fluorinated halopropanes. The preferred temperature, contact time, and reactant ratios depend on the catalyst in use and how long it has been on stream.

While many of the experiments reported used propylene as the feed hydrocarbon, propane can be used with similar effectiveness.

General Procedure for Chlorofluorination of Propane/Propylene

The reactor was an Inconel tube with an outside diameter of 0.5 inch (1.27 cm), shaped like a squared U. It was charged with the desired amount of catalyst, usually 20 ml, and purged with nitrogen. The reactor temperature was increased via a heated fluidized sand bath to 450° C. The nitrogen flow was maintained through the reactor during the heating period. When a temperature of about 450° C. was achieved, the HF flow was initiated and the nitrogen flow was discontinued. The temperature was then adjusted to the desired value. The HF flow was decreased to the desired value followed by initiating the chlorine and propane (or propylene) flow at the desired value. Alternatively, after heating the catalyst at 450° C., the temperature was lowered to 150° C. A $N_2$/HF flow was started over the catalyst and the temperature slowly raised to the reaction temperature.

GENERAL PROCEDURE FOR PRODUCT ANALYSIS

Product analysis was achieved by gas chromatography using a 3 meter column from Supelco, Inc., packed with 5% Krytox ® fluorocarbon oil supported on Carbopack ® B graphite carbon black. Sample injection was accomplished by an on line sample valve. The analysis was done at 70° C. for 8 minutes followed by temperature programming at 8 degrees per minute up to 200° C. and holding at 200° C. for an additional 16 minutes. Product analyses are reported as relative area %.

General Procedure for Preparing Catalyst $MCl_x/C$ (C herein represents carbon, M represents metal, and x is the valence of M)

The desired amount of metal chloride was dissolved in 35 to 75 ml of water and the entire solution poured over 40 cc of commercial carbon granules (Girdler 411, 0.32 cm pellets). The resulting mixture was allowed to stand at room temperature for one hour and was then placed in a vacuum oven at 110° C. for 16 to 24 hours to remove the water. The catalyst was then pretreated by heating in an atmosphere of nitrogen gas at 450° C. followed by heating in HF at 450° C. prior to its use as a chlorofluorination catalyst.

Catalyst Preparation

The following catalysts were prepared by the general procedure for $MCl_x/C$:

| Catalyst | Starting Material |
|---|---|
| $CoCl_2/C$ | 35 g $CoCl_2.6H_2O$/35 cc $H_2O$ |
| $FeCl_3/C$ | 39.7 g $FeCl_3.6H_2O$/35 cc $H_2O$ |
| $ZnCl_2/C$ | 20.44 g $ZnCl_2$/75 cc $H_2O$ |
| $ZrOCl_2/C$ | 37.53 g $ZrOCl_2$/75 cc $H_2O$ |
| $NiCl_2/C$ | 34.94 g $NiCl_2.6H_2O$/35 cc $H_2O$ |
| $LaCl_3/C$ | 62.43 g $LaCl_3.7H_2O$/75 cc $H_2O$ |
| $(ZnCl_2 + CoCl_2)/C$ | 30 g $ZnCl_2$/35 g $H_2O$ |
| $(AlCl_3 + CoCl_2)/C$ | 3.62 g $AlCl_3$/35 g $H_2O$ |
| $(CaCl_2 + CoCl_2)/C$ | 0.71 g $CaCl_2$/35 g $H_2O$ |
| $(CuCl_2 + CoCl_2)/C$ | 2.56 g $CuCl_2.2H_2O$/35.0 g $CoCl_2.6H_2O$/75 cc $H_2O$ |
| $(KCl + CoCl_2)/C$ | 1.12 g $KCl$/35 g $CoCl_2.6H_2O$/75 cc $H_2O$ |
| $(LaCl_3 + CoCl_2)/C$ | 5.57 g $LaCl_3.7H_2O$/35 g $CoCl_2.6H_2O$/75 cc $H_2O$ |

Preparation of Cr-oxide $AlF_3$ $CrCl_3.6H_2O$, 134 g, was dissolved in 1000 cc $H_2O$. To this solution was added 45g of $AlF_3$. The slurry was stirred and heated to 90° C. The pH of the hot solution was adjusted to 9 with concentrated ammonium hydroxide. The solution was stirred for one hour at 90° C. and then allowed to cool to room temperature. The crude solid was filtered, washed five times with 100 cc of $H_2O$ and dried in the vacuum oven at 110° C. The catalyst was mixed with 1-5 weight "Sterotex" powdered lubricant (registered trademark of Capital City Products Co., Columbus, Ohio, division of Stokely-Van Camp, for its edible hydrogenated vegetable oil) to give ⅛" diameter×3/16" long cylindrical pellets from a Stokes tablet machine.

Preparation of $La_{0.7}Sr_{0.3}CrO_{0.7}F_{0.6}$ $La(NO_3)_3.6H_2O$, 303.1 g, 400.2 g of $Cr(NO_3)_3.9H_2O$ was dissolved in 1000 cc of $H_2O$. The pH of the solution was adjusted to 9 with concentrated ammonium hydroxide. $SrF_2$, 37.7 g, was added and the slurry was stirred for 30 minutes. The crude solid was collected by filtration, washed with 500 cc of $H_2O$ and dried in a vacuum oven. The catalyst was fired 4 days at 600° C. with daily grinding and mixing. The catalyst was mixed with 1-5 weight % "Sterotex" powdered lubricant to give ⅛" diameter×3/16" long cylindrical pellets from a Stokes tablet machine.

Preparation of $CoCl_2$/Co-oxide $CoCl_2.6H_2O$, 95.17 g, was dissolved in 1000 cc of $H_2O$. The pH of the solution was adjusted to 9 with concentrated ammonium hydroxide. The slurry was allowed to stand overnight. The crude solid was collected by filtration, washed with $H_2O$ and dried in a vacuum oven.

100 g of this catalyst was slurried in 500 cc of 0.4 M solution of $CoCl_2$ for 30 minutes. The water was removed on a rotary evaporator and the crude solid dried in a vacuum oven. The catalyst was mixed with 1-5 weight % "Sterotex" powdered lubricant to give ⅛" diameter×3/16" long cylindrical pellets from a Stokes tablet machine.

Preparation of $Cr_2O_3LaAlO_3$

One liter of one molar $La(NO_3)_3$ and one liter of one molar $Al(NO_3)_3$ were combined. The volume of the solution was reduced to 500 cc via the rotory evaporator. The solution was poured into crucibles and placed in the vacuum oven at 110° C. for three days. The crude solid was ground up and placed back into the oven overnight. The solid was then fired at 1000° C. for 100 hours. A 100 g of this solid was slurried in a solution of 15.38 g of $Cr(NO_3)_3$ in 500 cc of distilled $H_2O$ for one hour. The water from the solution was removed on a rotory evaporator and the crude solid was dried in a vacuum oven and fired at 400° C. for one hour. The catalyst was mixed with 1-5 weight % "Sterotex" powdered lubricant to give ⅛" diameter× 3/16" long cylindrical pellets from a Stokes tablet machine.

Dehydration of $Cr_2O_3$ Catalysts

When hydrous chromium oxide is used in making a catalyst, that catalyst is preferably heated to 450° C. for about one hour with a flow of a gaseous diluent such as nitrogen, to dehydrate the hydrous chromium oxide (preferably low alkali metal content) before the catalyst is used.

Dehalogenation (Synthesis of Hexafluoropropylene)

The possibilities for the dehalogenation of $CF_3$—$CFCl$—$CF_3$ to hexafluoropropylene include (i) hydrogenation and (ii) reaction with a suitable metal.

i) Hydrogenation

While any hydrogenation catalyst could be used, the most active catalysts, such as Pt and Pd, are poor selections because, in addition to the desired products, they lead to the addition of hydrogen across any double bond present or to the substitution of hydrogen for chlorine, thus reducing the yield of desired products and requiring recycle. These effects are not desirable, but do not substantially reduce the overall yield to hexafluoropropylene, because the hydrogen-containing by-products can be recycled to the chlorofluorination step. Even catalysts containing excessive amounts of Ni can give this somewhat undesirable result.

Catalysts which are preferred include, as charged to the reactor, common hydrogenation catalysts such as Cu, Ni, Cr, or combinations thereof, optionally promoted with compounds of Mo, V, W, Ag, Fe, K, Ba, or combinations thereof. It is not critical whether the catalysts are supported or not, but some of the better catalysts include unsupported copper chromite. However, supports which are unreactive to halocarbons, HF, and oxygen at hydrogenation temperatures and up to 100° higher such as metal fluorides, alumina, and titania, may be used. Particularly useful are supports of fluorides of metals of Group II of the Mendeleeff periodic table, particularly Ca. A preferred catalyst is made of 1 15 equimolar quantities of Cu, Ni, and $Cr_2O_3$ on $CaF_2$.

An especially preferred catalyst contains 1.0 mole CuO, 0.2–1 mole NiO, 1–1.2 moles $Cr_2O_3$ on 1.3–2.7 moles of $CaF_2$, promoted with 1–20 weight %, based on the total catalyst, of an alkali metal selected from K, Cs, and Rb, preferably K. When K is the promoter, the preferred amount is 2–15 weight % of the total catalyst, but the method of adding the K is not critical. For example, it may be added as a salt or base.

This catalyst is not only useful for the reaction $CF_3—CFCl—CF_3 + H_2 \rightarrow CF_3CF=CF_2$, but also for corresponding hydrodehalogenations $CFCl_2—CF_2Cl + H_2 \rightarrow CFCl=CF_2$ and $CF_2Cl—CF_2Cl + H_2 \rightarrow CF_2=CF_2$.

The catalyst is prepared by coprecipitating, from an aqueous medium, salts of copper, nickel and chromium with and preferably on calcium fluoride; washing, heating, filtering and drying the precipitate; followed by depositing an alkali metal salt on the precipitate; and calcining the precipitate to convert the copper, nickel and chromium to the respective oxides. Copper, nickel and chromium salts suitable for use herein include the chlorides, fluorides and nitrates, with the nitrates being especially preferred.

The catalyst may be granulated, pressed into pellets, or shaped into other desirable forms. The catalyst may contain a binder to help ensure the physical integrity of the catalyst during granulating or shaping the catalyst into the desired form. Suitable binders include carbon and graphite, with carbon being preferred. When a binder is added to the catalyst, it normally comprises about 0.1 to 5 weight percent of the weight of the catalyst.

Another group of catalysts which showed good lifetime in the hydrodehalogenation of $CF_3—CFCl—CF_3$, $CF_2Cl—CF_2Cl$, or $CFCl_2—CF_2Cl$ is 1.0 CuO/0.2–1 NiO/1–2 $Cr_2O_3$/0.4–1 $MoO_3$/0.8–4 $CaF_2$, optionally promoted with at least one compound from the group consisting of $MgF_2$, $MnF_2$, and $BaF_2$ or with a trace of Pd or $WO_3$. Two of these hydrodehalogenation runs were shut down after 153 and 361 hours, respectively, while still giving good results.

After it is charged to the reactor, the hydrogenation catalyst is reduced with hydrogen at or somewhat above the desired reaction temperature before the chlorofluorocarbon feed is started.

After use in the hydrogenation reaction for a period of time, the activity of the catalyst may decrease. When this occurs, the catalyst activity can be regenerated by stopping the flow of halocarbon, flushing the bed with a gas such as hydrogen, air, or oxygen, at a temperature near or up to 100° higher than the hydrogenation temperature for at least several minutes. After the flushing step, the reactor temperature is readjusted to the hydrogenation temperature before resuming the hydrogenation reaction. While the inventors do not wish to be bound by any hypothesis, it is believed possible that catalyst activity deteriorates when the halocarbon feed deposits a small amount of polymer on the catalyst. Heating to a higher temperature in the presence of a flowing gas may pyrolyze the polymer to volatile fragments, which are swept away by the gas. The nature of the gas is not critical, but hydrogen is preferred.

A suitable temperature for the hydrogenation step is 250–550° C., preferably 350–475° C., and most preferably 400–450° C. A suitable contact time is 0.1–120 seconds. A preferred contact time is 0.3–60 seconds, and the most preferred contact time is 0.5–15 seconds.

Suitable pressure for the hydrogenation of $CF_3—CFCl—CF_3$ is 0–100 atmospheres gauge. Preferred is 0–50 atmospheres, and most preferred is 2–30 atmospheres.

As those skilled in the art appreciate, there is a relationship between catalyst activity, temperature, pressure, and contact time such that more active catalyst and higher pressure permit operation at lower temperature and shorter contact time.

ii) Dehalogenation with a metal

The elements of $Cl_2$ or ClF can be removed from a halocarbon using a metal such as Zn, Mg, Cu, Fe, or Ni or a combination of such metals. It is preferable to use Zn. It is also preferable to use a polar organic solvent for this reaction, such as an alcohol, ether, dioxane, anhydride, or nitrile. The temperature may be 25–200° C., preferably 70–200° C., and the time of reaction, which depends on the reagent and the temperature, can be determined by routine experimentation.

EXAMPLES

In all of the Examples herein:

Yield, as reported in the examples, is calculated from peak areas obtained in gas chromatographic analysis. This is a common technique in product identification, even though various compounds have different response factors.

Conversion of hydrocarbon in all chlorofluorination reactions is complete. Conversion to a particular product in the examples is calculated from peak areas obtained in gas chromatographic analysis.

Temperature in a tubular reactor of less than about 1 cm in diameter is measured with a thermocouple in the heat transfer medium outside the tube. Temperature in a tubular reactor of more than 1 cm diameter is measured with a thermocouple in an internal well. In large scale reactors, there are several thermocouples in the well so that the temperature profile can be observed.

EXAMPLES 1–16

The conditions and results of propylene chlorofluorination experiments directed toward $CF_3—CCl=CCl_2$ are recorded in Table I, in which Ct means contact time in seconds, and other abbreviations are defined.

Examples 1–9 are especially preferred for making $CF_3—CCl=CCl_2$.

In chlorofluorination experiments leading to $CF_3—CCl=CCl_2$ it is possible to replace part of the diluent HF and chlorine with three-carbon halocarbons which are underhalogenated or contain hydrogen. This kind of recycling is important to obtain maximum overall yields. Lower halocarbons containing only one or two carbon atoms may also be used as inert diluents for the chlorofluorination, and may be recycled repeatedly. Any gas which is inert to the reactants and products at reaction conditions is a candidate for use as a diluent in the chlorofluorination step.

Conversion of $CF_3—CCl=CCl_2$ to $CF_3—CFCl—CF_3$ was carried out by chlorofluorination using chromium oxide catalyst at a contact time of 16 seconds, using a temperature of 300–500° C., preferably 400–500° C., as shown in FIG. 1. With this catalyst and contact time, temperatures in the range of 300–400° C. give some of the desired product, but they also give large quantities of underfluorinated products, which have to be recycled. At 400° C., only $CF_3$—$CCl_2$—$CF_3$ has to be recycled. At 450° C., a higher conversion to the desired intermediate is obtained. At 500° C., $CF_3$—$CFCl$—$CF_3$ is the predominant product, but some perfluoropropane is formed and represents a yield loss unless there is a use for the saturated by-product.

This same kind of approach can be used with other catalysts and other contact times to select the best temperature for a given chlorofluorination reaction. Other catalysts that are very suitable for this reaction are chromium oxide on alumina, nickel chloride on alumina, and $Cr_5/Mn_5O_2$.

For the dehalogenation of $CF_3$—$CFCl$—$CF_3$, there are several examples.

i) Hydrogenation

EXAMPLE 22

A 1:1 molar mixture of hydrogen and $CF_3$—$CFCl$—$CF_3$ was passed over a $BaCrO_4$-modified copper chromite catalyst at 400° C. and atmospheric pressure at a contact time of 15–20 seconds. In several experiments, the once-through conversion to hexafluoropropylene was 60–70%, with $C_3F_7H$ the major by-product. This could be recycled to step (a) for further chlorination, so the overall yield was estimated to be excellent.

EXAMPLES 23–25

For these examples, an Inconel 600 U-tube reactor was made from 24 inches (61 cm) of 0.5 inch (1.3 cm) tubing. Each arm of the U-tube was 8 inches (20.3 cm) long, as was the bottom. The inlet and outlet to the reactor were ¼ inch (0.64 cm) tubing, and tees allowed ⅛ inch (0.32 cm) thermowells to be placed in each end of the tube. The reactor tube was totally filled with catalyst so that as the cool feed gases were heated, they were in contact with the catalyst. The inlet thermowell indicated that the gases were at reaction temperature within the first 4 inches (10.2 cm) of the reactor length. Because of the preheat length and the length of tubing above the level of the alundum, the actual heated length of the reactor was assumed to be 12 inches (30.5 cm). A separate thermocouple was kept in the fluidized bath to verify the batch temperature.

The cooled product from the reactor was passed into a small polypropylene trap, then into a 20% KOH scrubber made of polypropylene. The heat of reaction of HF and HCl with the alkali was never great enough to heat the solution above 50° C. The product then went through a water scrubber, a small bed of Drierite$^R$, and then to a cold trap in dry ice/acetone where the products and unconverted reactants were collected.

The main analysis tool used for this work was a temperature programmable Hewlett-Packard 5880A gas chromatograph with a thermal conductivity detector. This dual column unit was equipped with a pair of 8-foot × ⅛ inch (2.43 m × 0.32 cm) stainless steel columns packed with 1% SP-1000 on 60/80 mesh Carbopack B purchased from Supelco, Inc (catalog no. 1-2548). These columns were run with helium flows of 30 cc/minute. The column was started at 50 C for three minutes, then heated to 150° C. at a rate of 20° C./minute, and held there for another 15 minutes if necessary.

Three methods were employed in preparing the various catalysts:

A. Pyrolysis of nitrates. In this method the ingredients such as commercial copper chromite, chromium nitrate, $MoO_3$, etc., were prepyrolyzed in a resin kettle until all the removable water and volatiles were gone, and then the residue was calcined at 650° C. for at least three hours, usually overnight.

B. The various metal cations were precipitated from aqueous solution by adding KOH and KF solutions. The crude solids were filtered, washed well with water, prepyrolyzed and calcined as above.

B*. This method was similar to B, except that precipitation was sequential, rather than simultaneous. Typically, $CaF_2$ was precipitated first, allowed to age at least 24 hours, and only then were the hydrated oxides of transition metals precipitated onto the $CaF_2$ particles.

Several dozen catalysts were evaluated, and most of them gave 80–97% conversion from $CF_3$—$CFCl$—$CF_3$ to hexafluoropropylene. Three of the best runs are presented as Examples 23, 24, and 25.

The catalyst for Example 23 was $CuO/Cr_2O_3/NiO/0.9 MoO_3/2.1 CaF_2$, made by method B.

Example 24 used $CuO/NiO/Cr_2O_3/2.7CaF_2$ catalyst, prepared by method B*, which performed for over 130 hours of intermittent hydrogenation, and was still active as the experiment was voluntarily terminated.

Example 25 used as catalyst $CuO/1.2 Cr_2O_3/0.9 NiO/1.7 CaF_2$, prepared by method A.

The results for these examples are shown in Table II.

Any by-products made in the hydrogenation step can be recycled to step (a), so they do not represent a yield loss.

Example 25A used pellets of a $CuO/NiO/Cr_2O_3/2.7CaF_3$ catalyst which had been soaked in KOH until they contained, after drying, 7.9 weight percent K. The yield to HFP at 400° C. or at 420° C. after extended operation was quite superior to that obtained with similar catalysts containing 0.08% or 0.1.2% K, and was slightly superior to that obtained with similar catalysts containing 4.6, 8.9, 9.6, and 15.1% K.

EXAMPLE 26

This hydrogenation was also carried out at elevated pressure. A reactor was made of Inconel tubing with inside diameter 0.19 inches (0.48 cm). The reactor was charged with 1.0 g of $CuO/NiO/Cr_2O_3/2.7CaF_2$, which was conditioned with hydrogen at atmospheric pressure at 550° C. for one hour. Then the reactor was pressurized with nitrogen and fed 95% pure $CF_3$—$CFCl$—$CF_3$ and hydrogen at 150–200 psig (1034–1379 kPa) continuously at 420° C. for 46 hours. The conversion of $CF_3$—$CFCl$—$CF_3$ was 20%, and the yield of hexafluoropropylene from converted $CF_3$—$CFCl$—$CF_3$ was 98–100%, ending at 100%.

For comparison, a similar run was made under similar conditions with the $Cu/Ni/Cr_2O_3$ catalyst of U.S. Pat. No. 2,900,423, which gave higher yield to hexafluoropropylene for the first 10 hours, after which the yield decreased sharply while the yield in the previous experiment was steady or increased.

ii) Reaction With a Suitable Reducing Metal

EXAMPLE 27

Into a one-liter autoclave containing a few steel bearings to facilitate agitation were place 65 g. zinc dust, 15 g. copper powder, and 250 ml. acetonitrile. The autoclave was cooled and charged with 100 g. of halocarbons, of which 96.3 g. was $CF_3$—$CFCl$—$CF_3$, 0.7 g. was hexafluoropropylene, and 1.2 g. was $C_3F_7H$. The autoclave was shaken for 8 hours at 150° C. After cooling to room temperature, the contents were vented slowly into a cylinder cooled to $-80°$ C. Gas chromatographic analysis of the product showed 55% of the $CF_3$—$CFCl$—$CF_3$ was converted. The yield to hexafluoropropylene was 29% and the yield to $C_3F_7H$ was 68%. This by-product can be chlorinated to $CF_3$—$CFCl$—$CF_3$ for recycle.

TABLE I

CHLOROFLUORINATION OF PROPYLENE - PREDOMINANT PRODUCT $CF_3CCl=CCl_2$

| EXAMPLE | CATALYST | TEMP. | CT | NF | $Cl_2$ | $C_3H_6$ | CONV TO $CF_3CCl=CCl_2$ |
|---|---|---|---|---|---|---|---|
| 1 | $CoCl_2$/C (10 g) | 350° | 0.09 | 60 | 25 | 4 | 86.7% |
| 2 | $FeCl_3$/C (15 g) | 460° | 0.11 | 55 | 25 | 2 | 87.8% |
| 3 | (KCl + $CoCl_2$)/C (10 g) | 400° | 6.00 | 53 | 26 | 3 | 80.0% |
| 4 | Co-carb/C (10 g) | 400° | 6.00 | 51 | 25 | 3 | 71.0% |
| 5 | $LaCl_3$/C (10 g) | 200° | 5.00 | 103 | 24 | 3 | 67.0% |
| 6 | ($AlCl_3$ + $CoCl_2$)/C (10 g) | 400° | 6.00 | 54 | 25 | 3 | 71.0% |
| 7 | ($CaCl_2$ + $CoCl_2$)/C (10 g) | 400° | 6.00 | 58 | 29 | 3.3 | 68.0% |
| 8 | ($CuCl_2$ + $CoCl_2$)/C (10 g) | 400° | 6.00 | 51 | 25 | 3 | 61.0% |
| 9 | ($LaCl_3$ + $CoCl_2$)/C (10 g) | 400° | 6.00 | 51 | 25 | 3 | 62.0% |
| 10 | $ZrOCl_2$/C (10 g) | 300° | 0.12 | 52 | 23 | 3 | 47.4% |
| 11 | $ZnCl_2$/C (10 g) | 445° | 0.07 | 50 | 30 | 3 | 42.7% |
| 12 | $CoCl_2$/Co-oxide (20 g) | 450° | 0.14 | 60 | 25 | 3 | 33.5% |
| 13 | $Cr_2O_3$/$LaAlO_3$ (15 g) | 450° | 0.04 | 140 | 100 | 10 | 33.0% |
| 14 | Cr-oxide/$AlF_3$ (15 g) | 450° | 0.14 | 45 | 18 | 1 | 26.4% |
| 15 | $La_{.7}Sr_{.3}CrO_{2.7}F_{.6}$ (23 g) | 250° | 0.28 | 52 | 26 | 3 | 25.2% |
| 16 | $NiCl_2$/C (10 g) | 320° | 0.02 | 280 | 150 | 10 | 28.0% |

| EXAMPLE | YIELD TO $CF_3CCl=CCl_2$ +R | CONV TO $CF_3CFClCF_3$ | YIELD TO $CF_3CFClCF_3$ +R |
|---|---|---|---|
| 1 | 90.3% | — | 98.7% |
| 2 | 90.2% | — | 100.0% |
| 3 | 90.0% | — | — |
| 4 | 79.0% | — | 90.0% |
| 5 | 96.0% | — | — |
| 6 | 73.0% | — | 100.0% |
| 7 | 72.0% | — | 96.0% |
| 8 | 65.0% | — | — |
| 9 | 68.0% | — | — |
| 10 | 51.4% | — | 100.0% |
| 11 | 48.5% | — | 99.9% |
| 12 | 85.5% | — | 97.8% |
| 13 | 64.4% | 1.0% | 97.8% |
| 14 | 62.6% | — | 98.6% |
| 15 | 52.1% | — | 94.4% |
| 16 | 77.9% | — | 99.2% |

The CT or contact time is in seconds and is defined as the ratio of the volume of catalyst (cc) to the total flow of gases (cc/minutes ÷ 60).
The figures for NF, $Cl_2$ and $C_3H_6$ are the flow rates for the individual gases and are expressed in cc/minute.
The conversion figures are the conversions obtained via a one time pass over the catalyst and the yields are based on recycle of intermediates R which could be recycled under the same or more drastic conditions.
R = recyclable intermediates.

TABLE II

CONVERSION OF $C_3F_7Cl$ TO $C_3F_6$

| EXAMPLE | 23 | 24 | 25 |
|---|---|---|---|
| Temperature, °C. | 399 | 400 | 402 |
| Hours after startup | 1.0 | 1.0 | 3.5 |
| Feed | | | |
| $CF_3CFClCF_3$ | 90% | 77% | 79% |
| $C_2F_5CF_2Cl$ | 7% | 21% | 17% |
| $CF_3CCl=CF_2$ | 2% | 0.9% | 0.7% |
| Product, excluding recovered reactant | | | |
| $C_3F_6$ | 27% | 45% | 49% |
| $C_2F_5$—$CF_2H$ | 0.5% | 0.6% | 0.6% |
| $CF_3$—CFH—$CF_3$ | 1% | 0.8% | 0.9% |
| Conversion of $CF_3$—CFCl—$CF_3$ | 31% | 60% | 63% |
| Yield from $CF_3CFClCF_3$ to $CF_3CF=CF_2$ | 96% | 98% | 97% |
| Contact time, seconds | 11 | 11 | 10 |

What is claimed is:

1. A process for the preparation of hexafluoropropylene comprising, under effective reaction conditions:
   (a) chlorofluorinating a member of the group consisting of propane, propylene and partially halogenated C-3 acyclic hydrocarbons, by contacting with hydrogen fluoride and chlorine in a hydrogen fluoride/chlorine ratio of about 1:7 in the presence of a metal-containing solid catalyst to produce $CF_3CCl=CCl_2$;
   (b) chlorofluorinating said $CF_3CCl=CCl_2$ by contacting with chlorine and hydrogen fluoride in the presence of a metal-containing solid catalyst to produce $CF_3CFClCF_3$; and
   (c) hydrodehalogenating said $CF_3CFClCF_3$ to hexafluoropropylene by contacting with hydrogen in the presence of a catalyst.

2. A process of claim 1 in which the catalyst used in step (c) for the hydrodehalogenation further comprises potassium.

3. A process of claim 1 wherein the metal-containing catalyst used in step (a) is a compound of cobalt, lanthanum and iron.

4. A process of claim 1 wherein the chlorofluorination of step (a) is carried out at a temperature of about from 100° to 550° C.

5. A process of claim 1 wherein the ratio of HF to chlorine used in the chlorofluorination in step (a) is about from 1.7 to 4.3.

* * * * *

UNITED STATES PATENT AND TRADEMARK OFFICE
CERTIFICATE OF CORRECTION

PATENT NO. : 5,043,491

DATED : August 27, 1991

INVENTOR(S) : Webster, et al.

It is certified that error appears in the above-identified patent and that said Letters Patent is hereby corrected as shown below:

In Table I, appearing at columns 11 and 12, the fifth column heading "NF" should read --HF--

In the second footnote to Table I, "NF" should read --HF--

In Claim 1, at column 12, line 8, "1:7" should read --1:1 to 7:1--

Signed and Sealed this

Twenty-first Day of September, 1993

Attest:

BRUCE LEHMAN

Attesting Officer

Commissioner of Patents and Trademarks